(12) United States Patent
Holmes et al.

(10) Patent No.: US 11,083,902 B2
(45) Date of Patent: Aug. 10, 2021

(54) BIOSENSOR PACKAGE

(71) Applicant: International Business Machines Corporation, Armonk, NY (US)

(72) Inventors: Steven Holmes, Ossining, NY (US); Bruce B. Doris, Slingerlands, NY (US); Hariklia Deligianni, Alpine, NJ (US); Roy R. Yu, Poughkeepsie, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 213 days.

(21) Appl. No.: 15/991,254

(22) Filed: May 29, 2018

(65) Prior Publication Data

US 2019/0366102 A1  Dec. 5, 2019

(51) Int. Cl.
*A61N 1/00* (2006.01)
*A61N 1/375* (2006.01)
*A61N 1/36* (2006.01)

(52) U.S. Cl.
CPC ....... *A61N 1/3758* (2013.01); *A61N 1/36064* (2013.01); *A61N 1/36067* (2013.01); *A61N 1/36071* (2013.01); *A61N 1/36082* (2013.01); *A61N 1/36128* (2013.01)

(58) Field of Classification Search
CPC ............ A61B 5/04001; A61N 1/36121; A61N 2005/063; A61N 2005/0651; A61N 5/0622
See application file for complete search history.

(56) References Cited

U.S. PATENT DOCUMENTS

| 6,922,664 B1* | 7/2005 | Fernandez | G05B 23/0227 700/2 |
| 7,003,352 B1 | 2/2006 | Whitehurst | |
| 7,108,680 B2 | 9/2006 | Rohr et al. | |
| 7,147,865 B2* | 12/2006 | Fishman | A61N 1/0543 424/427 |
| 9,131,884 B2 | 9/2015 | Holmes et al. | |
| 9,743,870 B2 | 8/2017 | Wang et al. | |
| 10,493,297 B2* | 12/2019 | Seymour | A61N 5/0622 |

(Continued)

FOREIGN PATENT DOCUMENTS

| CN | 107543934 A | 1/2018 |
| EP | 1967581 A1 | 10/2008 |

OTHER PUBLICATIONS

Kozai et al. "Brain Tissue Responses to Neural Implants Impact Signal Sensitivity and Intervention Strategies", 2015, ACS Chemical Neuroscience, 2015, 6, 48-67 (Year: 2015).*

(Continued)

*Primary Examiner* — William R Carpenter
(74) *Attorney, Agent, or Firm* — Amin, Turocy & Watson, LLP

(57) ABSTRACT

Techniques regarding an implantable biosensor package are provided. For example, one or more embodiments described herein can regard an apparatus, which can comprise a biosensor module. The biosensor module can comprise a semiconductor substrate and a processor. The semiconductor substrate can have a sensor operably coupled to the processor. The apparatus can also comprise a polymer layer. The biosensor module can be embedded within the polymer layer such that the polymer layer can be provided on a plurality of sides of the biosensor module.

20 Claims, 10 Drawing Sheets

(56) References Cited

U.S. PATENT DOCUMENTS

| | | | |
|---|---|---|---|
| 2012/0122197 A1 | 5/2012 | Jospeh | |
| 2012/0226132 A1* | 9/2012 | Wong | A61B 5/0031 600/398 |
| 2014/0329707 A1* | 11/2014 | Naughton | A61B 5/04001 506/9 |
| 2015/0146203 A1 | 5/2015 | Lai et al. | |
| 2015/0362476 A1* | 12/2015 | Clements | G01N 21/01 506/10 |
| 2017/0095670 A1 | 4/2017 | Ghaffari et al. | |

OTHER PUBLICATIONS

Medical Design Briefs Magazine, "Bioactive Coating Camouflages Implants for Deep Brain Stimulation", 2012, Medical Design Briefs, Oct. 2012 Edition, p. 1 (Year: 2012).*

Vitale et al. "Biomimetic extracellular matrix coatings improve the chronic biocompatibility of microfabricated subdural microelectrode arrays", 2018, PLOS One, Nov. 2018, p. 1-19 (Year: 2018).*

Hayat et al. "Stealth functionalization of biomaterials and nanoparticles by CD47 mimicry", 2019, International Journal of Pharmaceutics, vol. 569, Oct. 5, 2019, 118628 (Year: 2019).*

International Search Report and Written Opinion received for PCT Application Serial No. PCT/IB2019/054165 dated Sep. 20, 2019, 9 pages.

Koh, et al., Glucose Sensor Membranes for Mitigating the Foreign Body Response, Journal of Diabetes Science and Technology, Sep. 2011, pp. 1052-1059, vol. 5, No. 5.

Lou, et al., Cross-linked hyaluronic acid hydrogel films: new biomaterials for drug delivery, Journal of Controlled Release, Jun. 22, 2000, pp. 169-189, vol. 69.

Iyer, et al., Virally mediated optogenetic excitation and inhibition of pain in freely moving non-transgenic mice, Nat Biotechnol., Mar. 2014, pp. 274-278, vol. 32 No. 3.

McCall, et al, Fabrication of flexible, multimodal light-emitting devices for wireless optogenetics, Nat Protoc., Dec. 2013, pp. 2413-2428, vol. 8, No. 12.

Montgomery, et al., Beyond the brain: Optogenetic control in the spinal cord and peripheral nervous system, Optogenetics, May 4, 2016, 13 Pages, vol. 8, No. 337.

Dave, et al., Sol-Gel Encapsulation Methods for Biosensors, Analytical Chemistry, Nov. 15, 1994, pp. 1120-1127, vol. 66, No. 22.

Seymour, et al., State-of-the-art MEMS and microsystem tools for brain research, Microsystems & Nanoengineering, Aug. 23, 2016, 16 Pages, vol. 3.

Stujenske, et al., Modeling the spatiotemporal dynamics of light and heat propagation for in vivo optogenetics, Cell Rep., Jul. 21, 2015, pp. 525-534, vol. 12, No. 3.

Ngoepe, et al., Integration of Biosensors and Drug Delivery Technologies for Early Detection and Chronic Management of Illness, Sensors, Jun. 14, 2013, vol. 13.

* cited by examiner

BIOSENSOR PACKAGE

BACKGROUND

The subject disclosure relates to biosensor package, and more specifically, to an implantable polymer package that can house one or more biosensor modules.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, apparatuses, and/or methods that can regard an implantable biosensor package are described.

According to an embodiment, an apparatus is provided. The apparatus can comprise a biosensor module comprising a semiconductor substrate and a processor. The semiconductor substrate can have a sensor operably coupled to the processor. The apparatus can also comprise a polymer layer. The biosensor module can be embedded within the polymer layer such that the polymer layer can be provided on a plurality of sides of the biosensor module.

According to another embodiment, another apparatus is provided. The apparatus can comprise a biosensor module comprising a semiconductor substrate and a processor. The semiconductor substrate can comprise an integrated stimulus device operably coupled to the processor. The apparatus can also comprise a polymer layer, wherein the biosensor module is embedded within the polymer layer such that the polymer layer is provided on a plurality of sides of the biosensor module.

According to another embodiment, a method is provided. The method can comprise injecting a polymer into a mold to generate a polymer layer. The method can also comprise attaching a biosensor module to the polymer layer such that the polymer layer is provided on a plurality of sides of the biosensor module. The biosensor module can comprise a semiconductor substrate and a processor. Also, the semiconductor substrate can have a sensor operably coupled to the processor.

DETAILED DESCRIPTION

Figure 1:
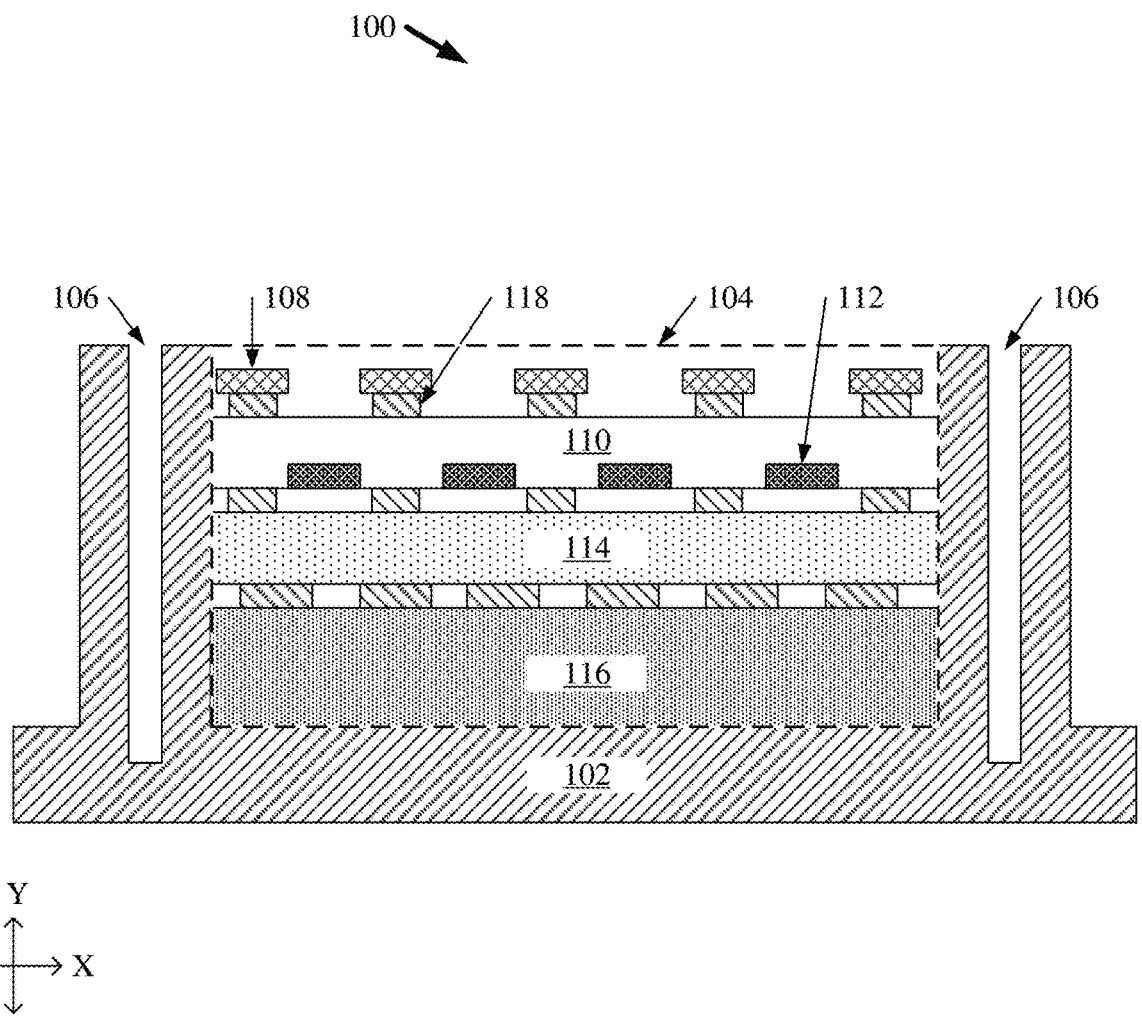
FIG. 1 illustrates a diagram of an example, non-limiting biosensor package that can be implanted into a host to facilitate monitoring and/or manipulation of the host's tissue in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details. Additionally, it is to be understood that various types of shading and/or cross-hatching presented within the drawings can delineate like features, like materials, and/or like compositions.

Traditional biosensors comprise one or more sensor devices located on a rigid semiconductor substrate. Typically, the biosensors are implanted into a host by plunging the biosensor directly into the host's tissue. The biosensors can detect various characteristics of the surrounding tissue and stimulate the tissue via various devices (e.g., via light emitting diodes ("LEDs")). However, plunging the biosensor into the host tissue can cause undesirable damage to the tissue. Further, the rigidity of traditional biosensors limits possible implant locations within the host. Also, traditional biosensor structures leave various components (e.g., the semiconductor substrate) unprotected from biological defense mechanisms, which can cause deterioration to the biosensor by the host. In addition, substantial direct exposure of various components (e.g., LEDs) to the host tissue can necessitate performance limitations (e.g., limitations on power usage to avoid overheating the tissue surround the biosensor).

Various embodiments described herein can regard an implantable package that can comprise one or more sensor modules embedded within a protective polymer. The one or more sensor modules can monitor and/or manipulate surrounding tissue while the polymer protects the one or more sensor modules from the hosts biological defense mechanisms and/or biological environment. Further, the polymer can be elastomeric, thereby providing flexibility to the implantable package. Due at least in part to the protective and flexible properties of the polymer, the one or more sensor modules can be manufactured using known electrical engineering techniques to achieve dimensions smaller than typical, bulky biosensors. In one or more embodiments, the implantable package can comprise a plurality of sensor modules to provide redundancies in case of mechanical failure and/or facilitate multiple functions. Moreover, in one or more embodiments the implantable package can further comprise one or more chemical delivery systems that can facilitate distribution of one or more chemicals to surrounding tissue.

FIG. 1 illustrates a diagram of an example, non-limiting biosensor package 100 from a cross-sectional viewpoint in accordance with one or more embodiments described herein. The biosensor package 100 can comprise a polymer layer 102, one or more biosensor modules 104 (e.g., indicated with a dashed line in FIG. 1), and/or one or more chemical delivery systems 106. The biosensor package 100 can be implanted into a biological environment, such as onto and/or into tissue (e.g., tissue of a host entity).

The polymer layer 102 can comprise a bioinert elastomeric polymer and can be provided on a plurality of sides of the one or more biosensor modules 104. For example, the polymer layer 102 can comprise one or more wall portions extending (e.g., in the "Y" direction) substantially perpendicular to a base portion (e.g., extending in the "X" direction), wherein the one or more biosensor module 104 can be located on top of the base portion and/or between the wall portions. For instance, as shown in FIG. 1, the polymer layer 102 can be provided on a left side, a right side, and a bottom side of the one or more biosensor modules 104. In one or more embodiments, the polymer layer 102 can surround the one or more biosensor modules 104. Also, in one or more embodiments the polymer layer 102 can encapsulate the one or more biosensor modules 104 (e.g., the polymer layer 102 can be further located on the top side of the one or more biosensor modules 104).

One of ordinary skill in the art will recognize that the dimensions of the polymer layer 102 can vary depending on the desired functions of the biosensor package 100, the type of polymer comprising the polymer layer 102, the biological environment the biosensor package 100 is expected to be implanted within, a combination thereof, and/or like. For example, a length of the polymer layer 102 (e.g., along the "X" direction) can range from, but is not limited to, greater than or equal to 5 micrometers (μm) to less than or equal to 180 μm. In another example, the height of the polymer layer 102 (e.g., along the "Y" direction) can range from, but is not limited to, greater than or equal to 1 millimeter (mm) and less than or equal to 2 mm. In a further example, the respective length (e.g., along the "X" direction) of the polymer layer's 102 one or more wall portions can range from, but is not limited to, greater than or equal to 30 μm and less than or equal to 1000 μm. In an additional example, the thickness of the polymer layer 102 can range from, but is not limited to, greater than or equal to 0.3 millimeters (mm) and less than or equal to 10 mm.

The polymer layer 102 can be characterized as being elastomeric, durable, bioinert, resistant to corrosion, an insulator, a combination thereof, and/or the like. Example polymers that can comprise the polymer layer 102 include, but are not limited to: polydimethylsiloxane ("PDMS"), polyurethane, chitin and/or similar bio-derived polymers, cellulose materials, a combination thereof, and/or the like. Also, the polymer layer 102 can be embedded with stable bio molecules (e.g., glycoproteins and/or myelin) so as to provide camouflage against biological defense mechanisms (e.g., immune systems). Further, in one or more embodiments, the polymer layer 102 can comprise tabs and/or protrusions that can be utilized to fix the biosensor package 100 to subject tissue.

The one or more biosensor modules 104 can be embedded within and/or fixed to the polymer layer 102. Further, the one or more biosensor modules 104 can comprise one or more sensors 108, one or more semiconductor substrates 110, one or more stimulus devices 112, one or more computer units 114, and/or one or more power devices 116.

The one or more sensors 108 can detect and/or monitor one or more conditions of the tissue and/or environment surrounding the biosensor package 100. The one or more detected and/or monitored conditions can regard, for example, one or more chemical and/or physical properties of the surrounding tissue and/or environment. Example conditions that can be detected and/or monitored by the one or more sensors 108 can include, but are not limited to: temperature, moisture content, pressure, light absorbance, electrical conductance, chemical species or biological information transmitters such as neurotransmitters, hormones, growth factors, metal ions such as Calcium, sodium and potassium, and pH, a combination thereof, and/or the like. Example devices that can comprise the one or more sensors 108 can include, but are not limited to: thermometers, piezoelectric materials, light sensors, pressure sensors, electrodes, chemical sensors such as electrodes sensitized to specific molecules, using fast scan cyclic voltammetry, field-effect transistor ("FET") sensors, bipolar junction transistor ("BJT") sensors, conductive organic electrodes imprinted with the target molecules, organic electrochemical transistor ("OECT") devices, fluorescence detectors, a combination thereof, and/or like. In one or more embodiments, the one or more sensors 108 can be optimized to monitor specific biomolecules. For example, one or more electrodes comprising the one or more sensors 108 can be coated with various polymers, which can be sensitive to respective biomolecules (e.g., such as polypyrrole, polyaniline, poly (3,4-ethylenedioxythiophene) ("PEDOT"), functionalized derivatives of PEDOT (e.g., methoxy, amine, alcohol, alkyl derivatives), imprinted with the target molecules, and/or glassy carbon for use with fast scan cyclic voltametry).

In one or more embodiments, the one or more sensors 108 can be fixed to the one or more semiconductor substrates 110. Additionally, in one or more embodiments, the one or more sensors 108 can interact with the one or more semiconductor substrates 110 through one or more vias 118. Further, the one or more sensors 108 can be positioned at various pitches ranging from, for example, greater than or equal to 300 nanometers (nm) and less than or equal to 1000 nm. Additionally, respective biosensor modules 104 can comprise various types of sensors 108. In other words, the one or more sensors 108 of a biosensor module 104 are not limited to a single type of device, nor are the functions of the one or more sensors 108 limited to a single function (e.g., detecting and/or monitoring a single type of condition).

The one or more semiconductor substrates 110 can support one or more features (e.g., the one or more sensors 108, the one or more stimulus devices 112, and/or the one or more computer units 114) of the one or more biosensor modules 104. Example materials that can comprise the one or more semiconductor substrates 110 can include, but are not limited to: silicon, germanium, silicon carbide, carbon doped silicon, compound semiconductors (e.g., comprising elements from periodic table groups III, IV, and/or V), silicon oxide, a combination thereof, and/or the like. For instance, the one or more semiconductor substrates 110 can be a bulk silicon wafer and/or a silicon-on-insulator ("SOI") wafer. Additionally, the one or more semiconductor substrates 110 can comprise electronic structures such as isolation wires (not shown). Further, the one or more semiconductor substrates 110 can be characterized by one or more crystalline structures. For example, the one or more semiconductor substrates 110 can comprise silicon <100>, silicon <110>, and/or silicon <111>, as described using Miller indices. Additionally, in one or more embodiments the one or more semiconductor substrates 110 can be transparent and/or semi-transparent to facilitate operation of the one or more sensors 108 and/or the one or more stimulus devices 112. For instance, in one or more embodiments the one or more semiconductor substrates 110 can comprise silicon oxide. In another instance, in one or more embodiments the one or more semiconductor substrates 110 can comprise gallium nitride. Moreover, in one or more embodiments the semiconductor substrate 110 can comprise semiconductor minerals and/or gemstones, such as sapphire. One of ordinary skill in the art will readily recognize that the thickness of the one or more semiconductor substrates 110 can vary depending on: the composition of the one or more semiconductor substrates 110, the number of sensors 108, the number of stimulus devices 112, the desired function of the biosensor package 100, a combination thereof, and/or the like.

The one or more stimulus devices 112 can generate one or more forms of stimulus to manipulate and/or modify the tissue and/or environment surrounding the biosensor package 100. For example, the one or more stimulus devices 112 can stimulate (e.g., and thereby manipulate and/or modify) the tissue and/or environment surrounding the biosensor package 100 with electrical signals, vibrations, heat, light, a combination thereof, and/or like. Example stimulus devices 112 can include, but are not limited to: LEDs, piezoelectric devices (e.g., lead zirconate titanate ("PZT") devices), electrodes, magnetic inductors, optical fibers, pulsed electrodes, physical nanorods and/or tubes for piercing cell structures, a combination thereof, and/or the like. Additionally, respective biosensor modules 104 can comprise various types of stimulus devices 112. In other words, the one or more stimulus devices 112 of a biosensor module 104 are not limited to a single type of device, nor are the functions of the one or more stimulus devices 112 limited to a single function (e.g., emitting light). In one or more embodiments, the one or more stimulus devices 112 can comprise one or more LEDs that can, collectively, emit light of various frequencies. For instance, one or more of the LEDs of the biosensor module 104 can emit blue light and/or one or more other LEDs of the biosensor module 104 can emit red light.

In various embodiments, the one or more stimulus devices 112 can be integrated within the one or more semiconductor substrates 110. The one or more semiconductor substrates 110 can provide mechanical support to the one or more stimulus devices 112 and/or can facilitate one or more electrical connections between the one or more stimulus devices 112 and/or the one or more computer units 114. For example, the one or more semiconductor substrates 110 can comprise conductive material (e.g., conductive strips, transmission lines, nanowires, electrical wires, a combination thereof, and/or like) to facilitate operable coupling of various features (e.g., the one or more sensors 108, the one or more stimulus devices 112, the one or more computer units 114, and/or the one or more power devices 116). Further, the one or more vias 118 can also facilitate said operably couplings.

The one or more computer units 114 can comprise, for example, one or more processors to facilitate execution of one or more computer readable program instructions. Example computer units 114 can include, but are not limited to: microcontrollers, microprocessors, microcomputers, field-programmable gate arrays ("FPGA"), a combination thereof, and/or the like. The one or more computer units 114 can analyze data collected by the one or more sensors 108 and/or control the one or more stimulus devices 112 based on the analysis to achieve one or more objectives. The one or more computer units 114 can be operably coupled to the one or more sensors 108 and/or the one or more stimulus devices 112. For example, the one or more computer units 114 can be operably coupled to the one or more sensors 108 and/or the one or more stimulus devices 112 via one or more electrical connections (e.g., wires) and/or one or more vias 118 comprised within the semiconductor substrate 110. One of ordinary skill in the art will recognize that the dimensions of the one or more computer units 114 can vary depending on the desired functionality of the biosensor package 100. For example, the one or more computer units 114 can be comprised on a die size ranging from, but not limited to, greater than or equal to 100×100 µm and less than or equal to 1000×1000 µm.

The one or more power devices 116 can supply power (e.g., electricity) to the one or more sensors 108, the one or more stimulus devices 112, and/or the one or more computer units 114. Also, the one or more power devices 116 can be operably coupled (e.g., via one or more vias 118) to the one or more sensors 108, the one or more stimulus devices 112, and/or the one or more computer units 114. The one or more power devices 116 can comprise, for example, one or more capacitors and/or one or more batteries. In one or more embodiments, the one or more power devices 116 can be charged and/or re-charged wireless, for example, through the use of one or more inductors. Thus, the one or more power devices 116 can be charged and/or re-charged while implanted within the host.

The one or more chemical delivery systems 106 can be comprised within one or more wall portions of the polymer layer 102. The one or more chemical delivery systems 106 can comprise, for example, one or more microfluidic channels that can be loaded with one or more hydrogels (not shown). FIG. 1 illustrates chemical delivery systems 106 comprising microfluidic channels extending along the "Y" direction in straight paths; however, the architecture of the microfluidic channels is not so limited. For examples, the microfluidic channels can be characterized by various path architectures such as diagonal paths, zig-zag paths, and/or U-shaped paths. In one or more embodiments, a distal end of the one or more microfluidic channels comprising the chemical delivery systems 106 can be exposed to the tissue and/or environment surrounding the biosensor package 100. Thus, the polymer layer 102 can define a plurality of sides of the one or more chemical delivery systems 106 while leaving one or more sides of the chemical delivery systems 106 open to the surrounding tissue and/or environment.

As shown in FIG. 1, the one or more chemical delivery systems 106 can be located adjacent to the one or more biosensor modules 104. For example, the one or more chemical delivery systems 106 can flank one, two, three, and/or four sides of the one or more biosensor modules 104. One of ordinary skill in the art will recognize that the dimensions of the one or more chemical delivery systems 106 can vary depending on the desired volume of hydrogel to be loaded within the microfluidic channels. For example, the respective widths of the one or more microfluidic channels that can comprise the chemical delivery systems 106 can range from, but are not limited to, greater than or equal to 5 µm to less than or equal to 180 µm. The one or more chemical delivery systems 106 can be characterized by uniform dimensions; or alternatively, can be characterized by varying respective dimensions.

In one or more embodiments, the one or more chemical delivery systems 106 can be loaded with one or more hydrogels. The one or more hydrogels can comprise one or more chemical compounds to be distributed to the tissue and/or environment surrounding the biosensor package 100. For example, the hydrogels can react (e.g., dissolve and/or otherwise degrade) in the presence of the surrounding tissue and/or environment (e.g., due at least to one or more biological defense mechanisms of the host), and thereby released the one or more subject chemicals comprised within the hydrogel. Thus, the one or more subject chemicals can escape from the one or more chemical distribution systems 106 (e.g., via the one or more exposed sides) and/or interact with the surrounding tissue and/or environment. Further, respective chemical delivery systems 106 can house the same chemical compounds and/or respective chemical delivery systems 106 can comprise respective chemical compounds. Example chemical compounds that be comprised within the hydrogel and/or housed within the one or more chemical delivery systems 106 can include, but are not limited to: a genetic material (e.g., carried by a virus) for expression of a protein, a neural transmitter (e.g., dopamine, gamma-Aminobutyric acid ("GABA"), and/or serotonin), a growth factor, a growth inhibitor, a medicine (e.g., a medication for epilepsy and/or Parkinson's disease), a combination thereof, and/or the like.

Figure 2:
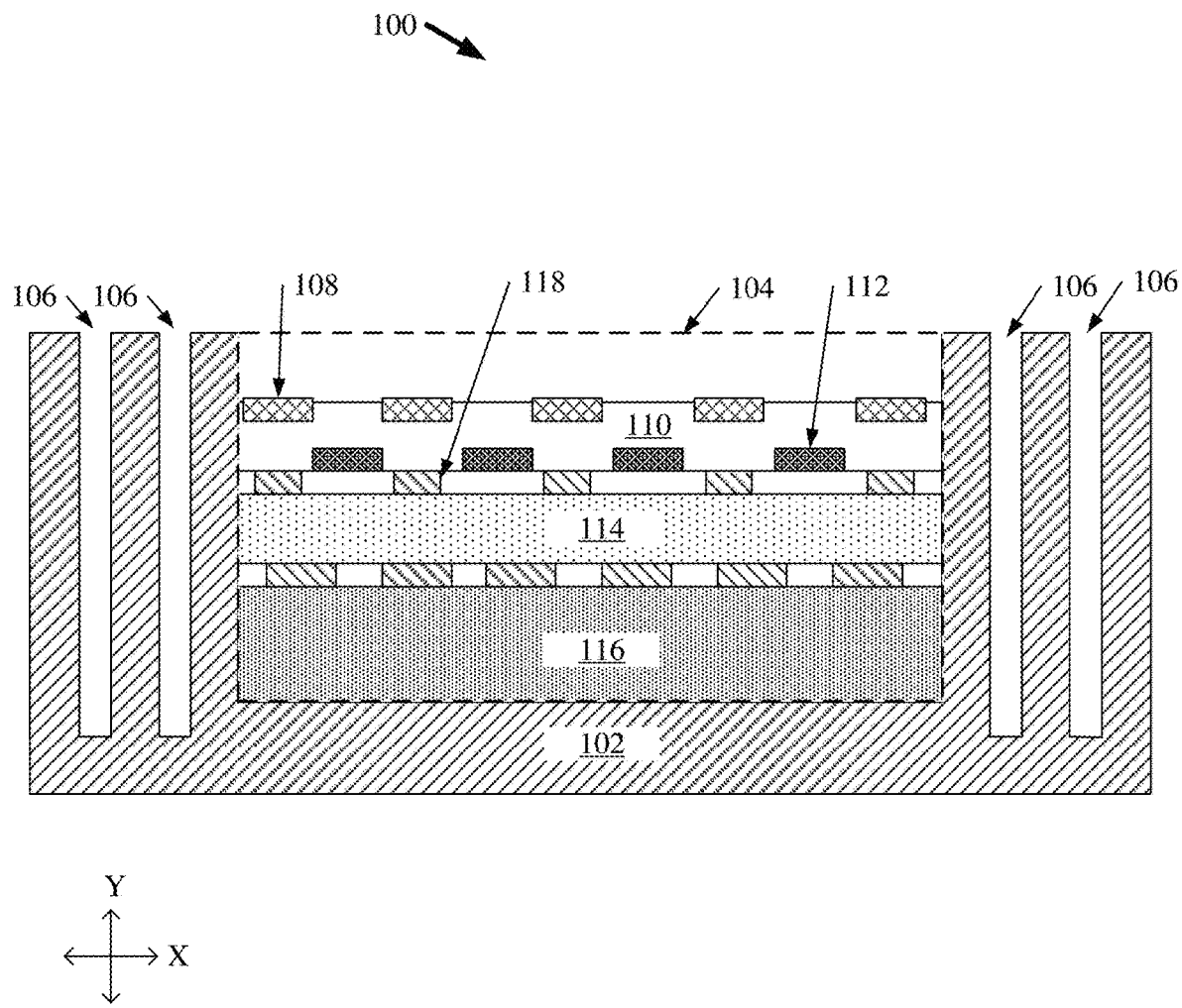
FIG. 2 illustrates a diagram of an example, non-limiting biosensor package that can comprise a plurality of chemical delivery systems in accordance with one or more embodiments described herein.

FIG. 2 illustrates a diagram of the example, non-limiting biosensor package 100 in accordance with one or more embodiments described herein. Repetitive description of like elements employed in other embodiments described herein is omitted for sake of brevity. FIG. 2 illustrates that one or more features of the one or more biosensor modules 104 other than the one or more stimulus devices 112 can be integrated into a single layer (e.g., the one or more semiconductor substrates 110).

For example, in one or more embodiments the one or more sensors 108 and the one or more stimulus devices 112 can both be integrated within the semiconductor substrate 110. For instance, the semiconductor substrate can comprise gallium nitride. Further, in various embodiments, the one or more computer units 114 can also be integrated into the one or more semiconductor substrates 110. Thus, while FIG. 1 depicts a biosensor module 104 structure comprising one or more sensors 108, one or more stimulus devices 112, and/or one or more computer units 114 on respective layers; one or more embodiments can comprise a biosensor module 104 structure wherein one or more of the one or more sensors 108, one or more stimulus devices 112, and/or one or more computer units 114 are integrated onto a common layer (e.g., integrated onto and/or into the one or more semiconductor substrates 110).

Furthermore, FIG. 2 illustrates that the biosensor package 100 can comprise numerous chemical delivery systems 106 located adjacent to a side of the one or more biosensor module 104. For example, two or more chemical delivery systems 106 can be located adjacent to a left side and/or a right side of the one or more biosensor modules 104, as shown in FIG. 2. On of ordinary skill in the art will recognize that the number of chemical delivery systems 106 comprised within the polymer layer 102 can varying depending on the function of the biosensor package 100 and/or the dimensions of the biosensor package 100.

Figure 3:
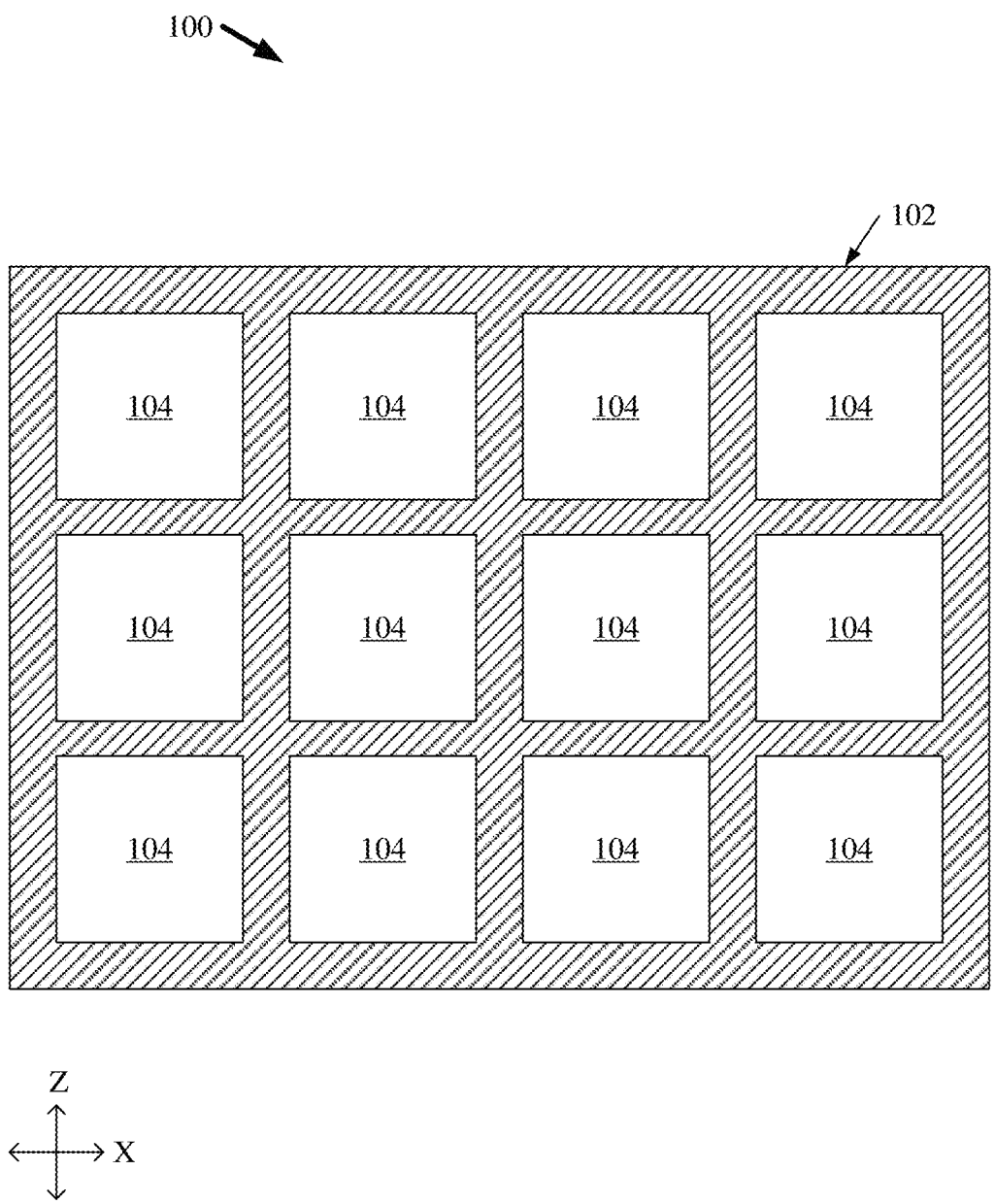
FIG. 3 illustrates a diagram of an example, non-limiting biosensor package that can comprise an array of biosensor modules in accordance with one or more embodiments described herein.

FIG. 3 illustrates a diagram of the example, non-limiting biosensor package 100 from a top point of view in accordance with one or more embodiments described herein. Repetitive description of like elements employed in other embodiments described herein is omitted for sake of brevity. As shown in FIG. 3, a plurality of biosensor modules 104 can be embedded within the polymer layer 102 and/or arranged in an array.

The wall portions of the polymer layer 102 can separate biosensor modules 104 from each other and/or facilitate containing the plurality of biosensor modules 104 within the polymer layer 102. The elastomeric quality of the polymer layer 102 can enable the biosensor package 100 to wrap around and/or otherwise bend around various tissue structures so as to provide an array of biosensor modules 104 across irregular surface areas. Also, by comprising an array of biosensor modules 104 (e.g., as shown in FIG. 3) the biosensor package 100 can comprise redundancies that can be utilized in the case of malfunctions. In other words, the biosensor package 100 can remain functional despite damage and/or malfunction of a biosensor module 104 due at least in part to the existence of one or more adjacent biosensor modules 104 that can perform the same and/or a similar task.

Moreover, in various embodiments one or more of the biosensor modules 104 comprising the array of biosensor modules 104 that can characterize the structure of the biosensor package 100 can perform one or more different functions than one or more other biosensor modules 104 within the array. For example, a first biosensor module 104 within the array can comprise different sensors 108 and/or stimulus devices 112 than a second biosensor module 104 within the array. Therefore, the biosensor package 100 can perform a variety of tasks due to respective performance capacities of respect biosensor modules 104 comprising the biosensor package 100.

One of ordinary skill in the art will recognize that the number of biosensor modules 104 comprising the biosensor package 100 can vary depending on the size of the biosensor modules 104, the size of the biosensor package 100, the one or more desired functions of the biosensor package 100, the number of chemical delivery systems 106, a combination thereof, and/or the like. While FIG. 3 illustrates twelve biosensor modules 104, the biosensor package 100 can comprise fewer or additional biosensor modules 104. For example, the number of biosensor modules 104 comprised within the biosensor package 100 can range from, but is not limited to, greater than or equal to 1 and less than or equal to 10,000.

Figure 4:
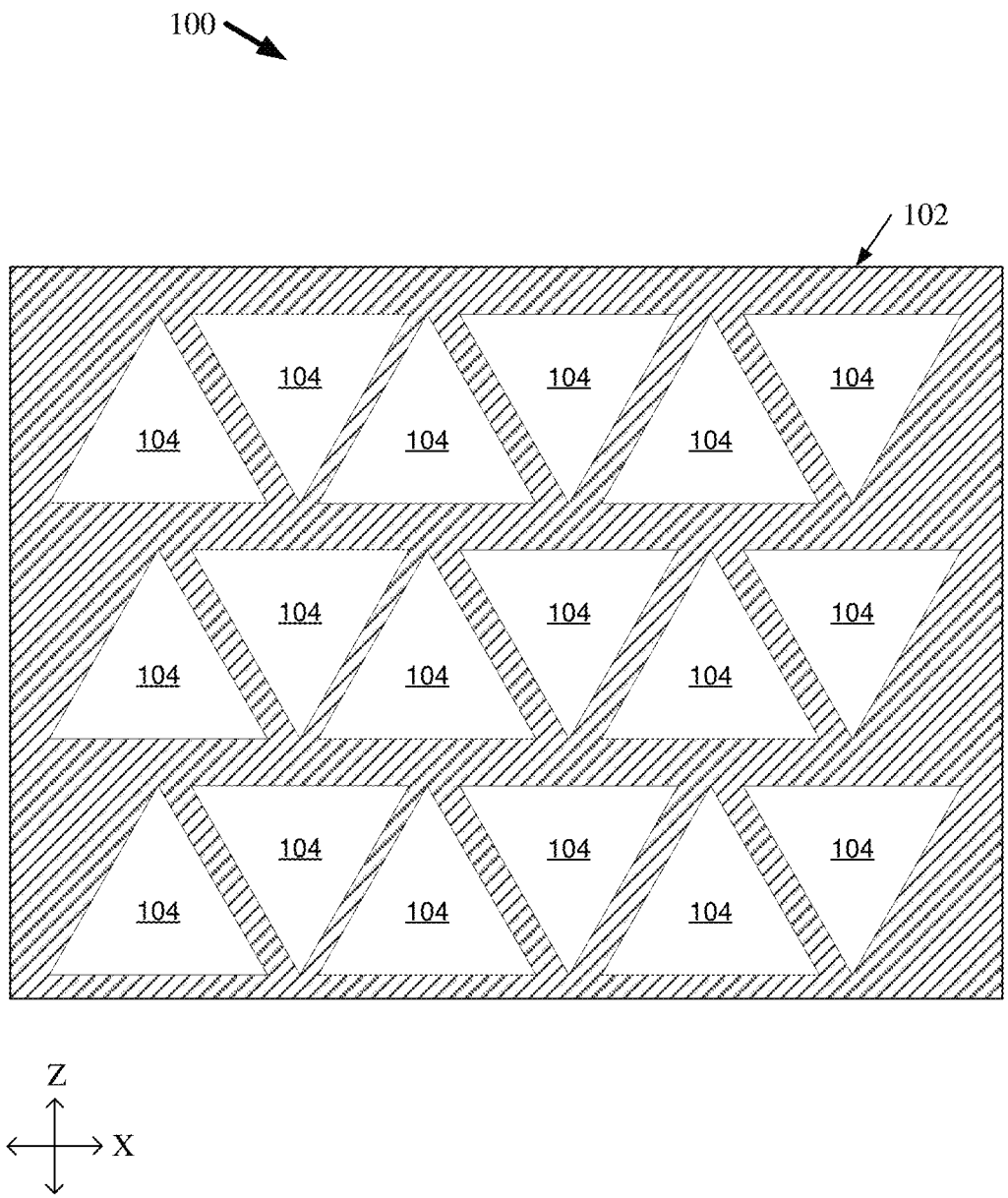
FIG. 4 illustrates another diagram of an example, non-limiting biosensor package that can comprise an array of biosensor modules in accordance with one or more embodiments described herein.

FIG. 4 illustrates another diagram of the example, non-limiting biosensor package 100 from a top point of view in accordance with one or more embodiments described herein. Repetitive description of like elements employed in other embodiments described herein is omitted for sake of brevity. As shown in FIG. 4, the one or more biosensor modules 104 can be characterized by a variety of shapes.

While FIG. 3 depicts the one or more biosensor modules 104 as having a square shape, FIG. 4 exemplifies that the one or more biosensor modules 104 can have alternate shapes such as a triangular shape. Different structural shapes can facilitate different functions and/or unique properties of flexibility. For example, various structural shapes can offer achieve respective concentrations of the biosensor modules 104 in the polymer layer 102. Example shapes that can characterize the structure and/or dimensions of the one or more biosensor modules 104 can include, but are not limited to: squares, rectangles, triangles, hexagons, pentagons, octagons, decagons, a combination thereof, and/or other polygons. Further, although FIGS. 3 and 4 depict biosensor module 104 arrays comprising uniform shapes, the architecture of the biosensor package 100 is not so limited. For instance, the biosensor package 100 can comprise an array of biosensor modules 104 characterized by a variety of shapes.

Figure 5:
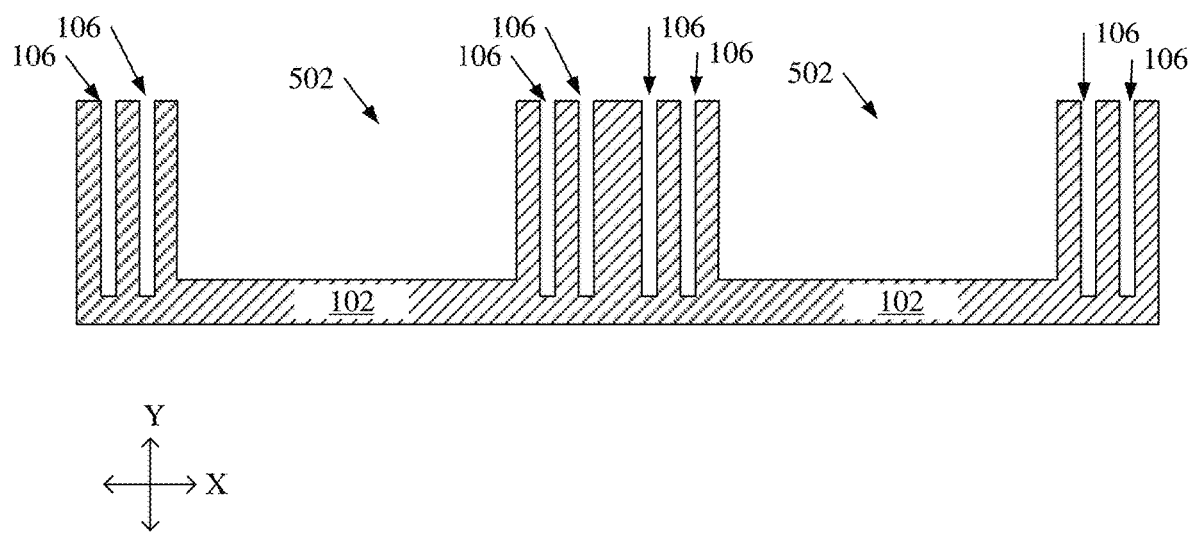
FIG. 5 illustrates a diagram of an example, non-limiting polymer layer that can house a plurality of biosensor modules and/or chemical delivery systems in accordance with one or more embodiments described herein.

FIG. 5 illustrates a diagram of the example, non-limiting polymer layer 102 from a cross-sectional view point in accordance with one or more embodiments described herein. Repetitive description of like elements employed in other embodiments described herein is omitted for sake of brevity. FIG. 5 depicts the biosensor package 100 prior to the inclusion of the one or more biosensor modules 104 during a manufacturing process.

As shown in FIG. 5, the polymer layer 102 can form one or more pockets 502 defined by the one or more wall portions. The one or more biosensor modules 104 can be inserted and/or fixed into the one or more pockets 502 to manufacture the biosensor package 100. Wherein the biosensor package 100 comprises an array of biosensor modules 104, the polymer layer 102 can comprise a plurality of pockets 502 positioned in the orientation and/or configuration of the array. Further, FIG. 5 illustrates that the polymer layer 102 can comprise one or more chemical delivery systems 106 adjacent to one or more of the pockets 502. For example, the one or more chemical delivery systems 106 can be located within the polymer layer 102 (e.g., defined by the polymer layer 102) and/or between adjacent pockets 502, and thereby between adjacent biosensor modules 104 in the biosensor package 100. As described herein, the number of chemical delivery systems 106 can vary and/or the architecture of the polymer layer 102 is not limited to four chemical delivery systems 106 between adjacent pockets 502, as shown in FIG. 5 (e.g., the biosensor package 100 can comprise fewer or additional chemical delivery systems 106 between adjacent biosensors modules 104 in an array). Further, while FIG. 5 depicts the one or more chemical delivery systems 106 having uniform dimensions, the architecture of the biosensor package 100 is not so limited. For example, respective chemical delivery systems 106 can be characterized by respective dimensions.

Figure 6:
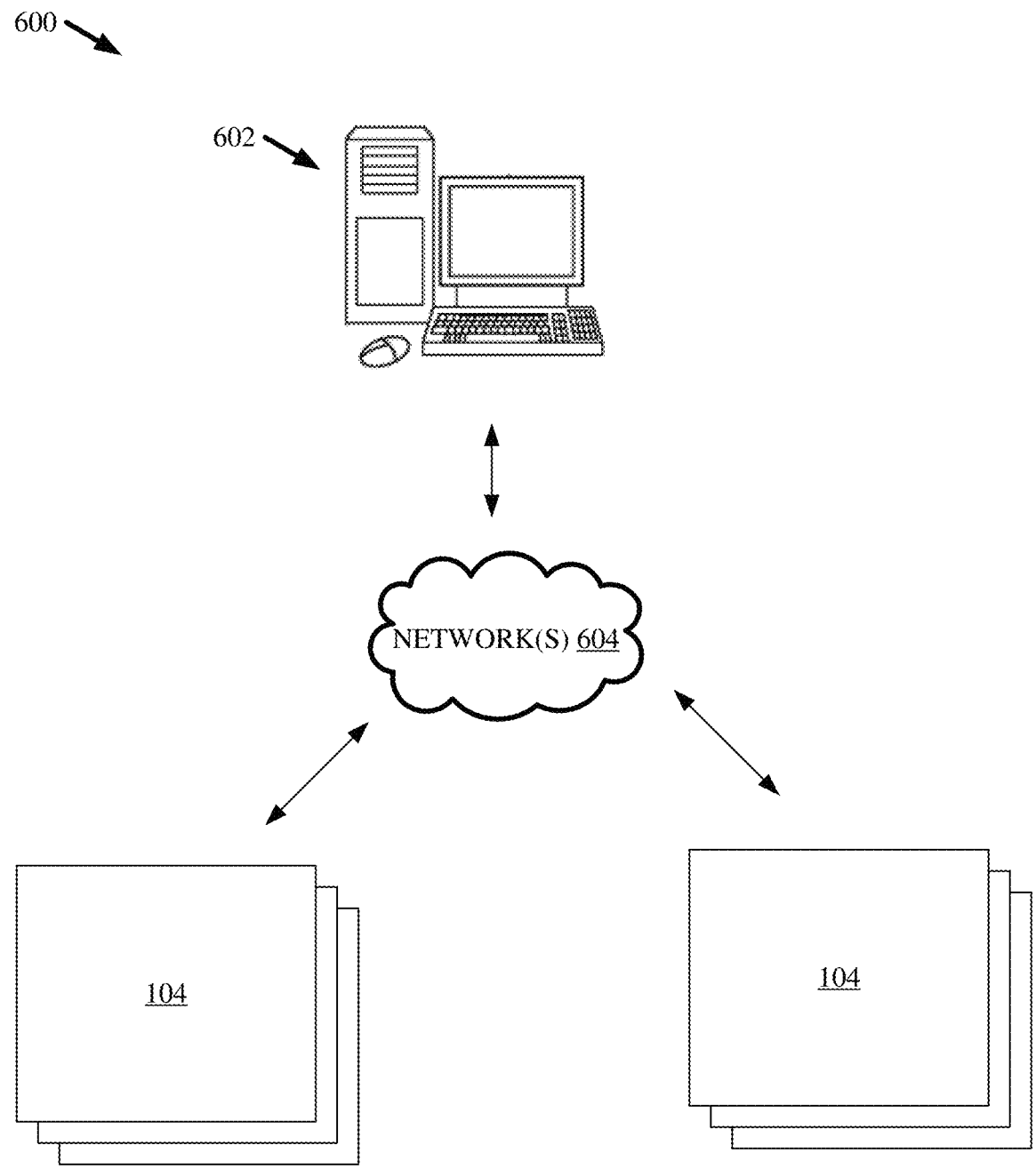
FIG. 6 illustrates a diagram of an example, non-limiting system that can comprise one or more biosensors packages in accordance with one or more embodiments described herein.

FIG. 6 illustrates a diagram of an example, non-limiting system 600 that can comprise one or more biosensor packages 100 in accordance with one or more embodiments described herein. Repetitive description of like elements employed in other embodiments described herein is omitted for sake of brevity. As shown in FIG. 6, one or more biosensor modules 104 can be operably coupled to one or more controllers 602 via one or more networks 604.

The one or more controllers 602 can comprise one or more computerized devices, which can facilitate a user of the system 600 to monitor and/or control the one or more biosensor modules 104. Example computerized devices that can comprise the one or more controllers 602 can include, but are not limited to: personal computers, desktop computers, laptop computers, cellular telephones (e.g., smart phones), computerized tablets (e.g., comprising a processor), smart watches, keyboards, touch screens, mice, a combination thereof, and/or the like. Additionally, the one or more controllers 602 can comprise one or more displays that can present one or more outputs generated by the system 600 (e.g., the one or more biosensor modules 104) to a user. For example, the one or more displays can include, but are not limited to: cathode tube display ("CRT"), light-emitting diode display ("LED"), electroluminescent display ("ELD"), plasma display panel ("PDP"), liquid crystal display ("LCD"), organic light-emitting diode display ("OLED"), a combination thereof, and/or the like. A user of the system 600 can send instructions (e.g., program instructions) to the one or more biosensor modules 104 and/or can view data (e.g., representing one or more conditions monitored and/or detected by the one or more biosensor modules 104) outputted by the one or more biosensor modules 104.

The one or more networks 604 can comprise wired and wireless networks, including, but not limited to, a cellular network, a wide area network (WAN) (e.g., the Internet) or a local area network (LAN). For example, the one or more controllers 602 can communicate with the one or more biosensor modules 104 (and vice versa) using virtually any desired wired or wireless technology including for example, but not limited to: cellular, WAN, wireless fidelity (Wi-Fi), Wi-Max, WLAN, Bluetooth technology, a combination thereof, and/or the like.

The one or more biosensor modules 104 can comprise one or more reception and/or transmission components, such as one or more antennas (e.g., factual antennas). The one or more reception and/or transmission components can be operably coupled to the one or more computer units 114 and/or the one or more power devices 116. Further, the one or more reception and/or transmission components can be protected by the polymer layer 102 from the biological environment surrounding the biosensor package 100. In one or more embodiments, the one or more reception and/or transmission component can be integrated into the one or more computer units 114. The one or more reception and/or transmission components can facilitate connection between the one or more biosensor modules 104 and/or the one or more networks 604, and thereby the one or more controllers 602. For example, the one or more biosensor modules 104 can, via the one or more networks 604, receive (e.g., from the one or more controllers 602) one or more instructions (e.g., program instructions) to be executed by the one or more computer units 114 and/or transmit (e.g., to the one or more controllers 602) data representing one or more operations of the biosensor module 104 and/or the biosensor package 100.

The one or more biosensor modules 104 can communicate with the one or more controllers 602 and/or with one or more other biosensor modules 104 (e.g., via the one or more networks 604). For example, the one or more biosensor modules 104 can communicate with other biosensor modules 104 comprising the same biosensor package 100. In another example, the one or more biosensor modules 104 of a first biosensor package 100 can communicate with one or more biosensor modules 104 of a second biosensor package 100.

The various embodiments of the biosensor package 100 described herein can facilitate treatment of various intractable health conditions such as chronic pain, depression, schizophrenia, epilepsy, diabetes, obesity, Parkinson's disease, and/or muscle tissue control. The biosensor package 100 can be implanted in one or more locations throughout a patient's body to manipulate, monitor, and/or modify desired segments of tissue. For example, the biosensor package 100 can be implanted into body regions that are typically difficult to reach, sensitive to intrusion, and/or subject to flexibility (e.g., due to motion). For instance, the biosensor package 100 can be implanted into brain regions, spinal regions, and/or nervous system regions.

In one or more embodiments, the biosensor package 100 can be utilized to facilitate one or more optogenetic methods of treatment. For example, the one or more biosensor modules 104 can act as optogenetic stimulation devices. One or more biosensor packages 100 can be fixed to a subject tissue segment via known medical techniques (e.g., stitches and/or medical adhesive). The one or more biosensor modules 104 can monitor one or more conditions of the surrounding tissue. Also, the one or more biosensor modules 104 can comprise one or more LEDs to stimulate the surrounding tissue using light. Moreover, the one or more chemical delivery systems 106 can be loaded with one or more chemical compounds that can facilitate manipulations of the surrounding tissue via light stimulation.

For example, the biosensor package 100 can be implanted into a brain section and/or the one or more chemical delivery systems 106 can be loaded with a hydrogel comprising: a virus carrying genetic material for the expression of opsin protein, and/or opsin protein itself. The biological environment surrounding the biosensor package 100 can dissolve and/or other degrade the hydrogel, thereby releasing the virus and/or opsin protein. The virus can infect one or more local neurons with the genetic material, thereby causing the neurons to produce opsin protein. The opsin protein (e.g., either released by the chemical delivery system 106 and/or produced by the neurons) can embed into the cellular membrane of the local neurons. The opsin protein can form an ion channel within the cellular membrane and be sensitive to light. For example, the opsin protein can open the ion channel in the presence of blue light and close the ion channel in the absence of light. The ion channel can facilitate a flow of ions and thereby control the electric potential of a subject neuron.

The one or more biosensor modules 104 can thereby control one or more functions of the local neurons by stimulating and/or not stimulating the opsin protein positioned within the local neurons. For example, by emitting blue light, the one or more biosensor modules 104 can affectively activate one or more local neurons. Conversely, by ceasing to emit blue light, the one or more biosensor modules 104 can affectively deactivate one or more local neurons. Said activation and/or deactivation can be controlled by the one or more controllers 602 (e.g., via the one or more networks 604) to achieve one or more treatment conditions. One of ordinary skill in the art will further recognize that the biosensor package 100 can be used for a variety of medical treatments in addition to optogenetic.

Figure 7:
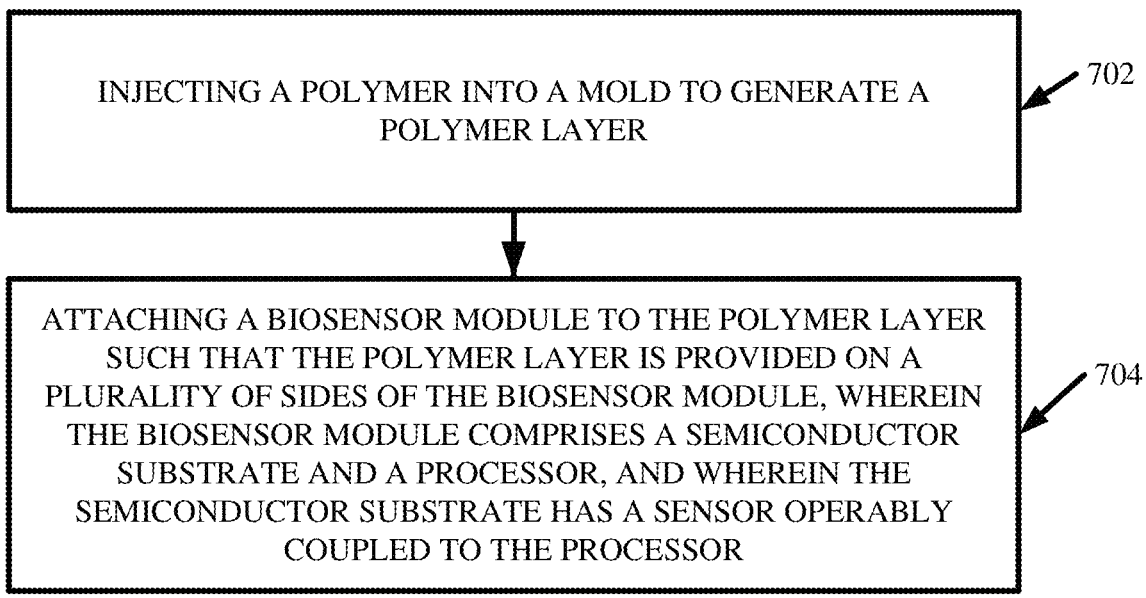
FIG. 7 illustrates a flow diagram of an example, non-limiting method that can facilitate manufacturing of one or more biosensor packages in accordance with one or more embodiments described herein.

FIG. 7 illustrates a flow diagram of an example, non-limiting method 700 that can facilitate manufacturing of one or more biosensor packages 100 in accordance with one or more embodiments in accordance with one or more embodiments described herein. Repetitive description of like elements employed in other embodiments described herein is omitted for sake of brevity.

At 702, the method 700 can comprise injecting a polymer (e.g., an elastomeric polymer) into a mold to generate a polymer layer 102. Example polymers that can be injected into the mold can include, but are not limited to: PDMS and/or polyurethane. The mold can facilitate structuring the polymer layer 102 into base portions and/or wall portions. The mold can also facilitate defining one or more chemical delivery systems 106 within the polymer layer 102. In one or more embodiments, the polymer can be hardened within the mold to achieve the desired structural formation. Subsequent to hardening the polymer, the polymer layer 102 can be released from the mold to facilitate further manufacturing of the one or more biosensor packages 100.

At 704, the method 700 can comprise attaching one or more biosensor modules 104 to the polymer layer 102 such that the polymer layer 102 can be provided on a plurality of sides of the one or more biosensor modules 104. The one or more biosensor modules 104 can comprise, for example: one or more sensors 108, one or more semiconductor substrates 110, one or more stimulus devices 112, one or more computer units 114 (e.g., which can include one or more processors), and/or one or more power devices 116. Further, one or more of the features of the one or more biosensor modules 104 (e.g., the one or more sensors 108 and/or the one or more computer units 114) can be operably coupled together. In one or more embodiments, the one or more biosensor modules 104 can be inserted and/or attached to one or more pockets 502 defined by the polymer layer 102.

Figure 8:
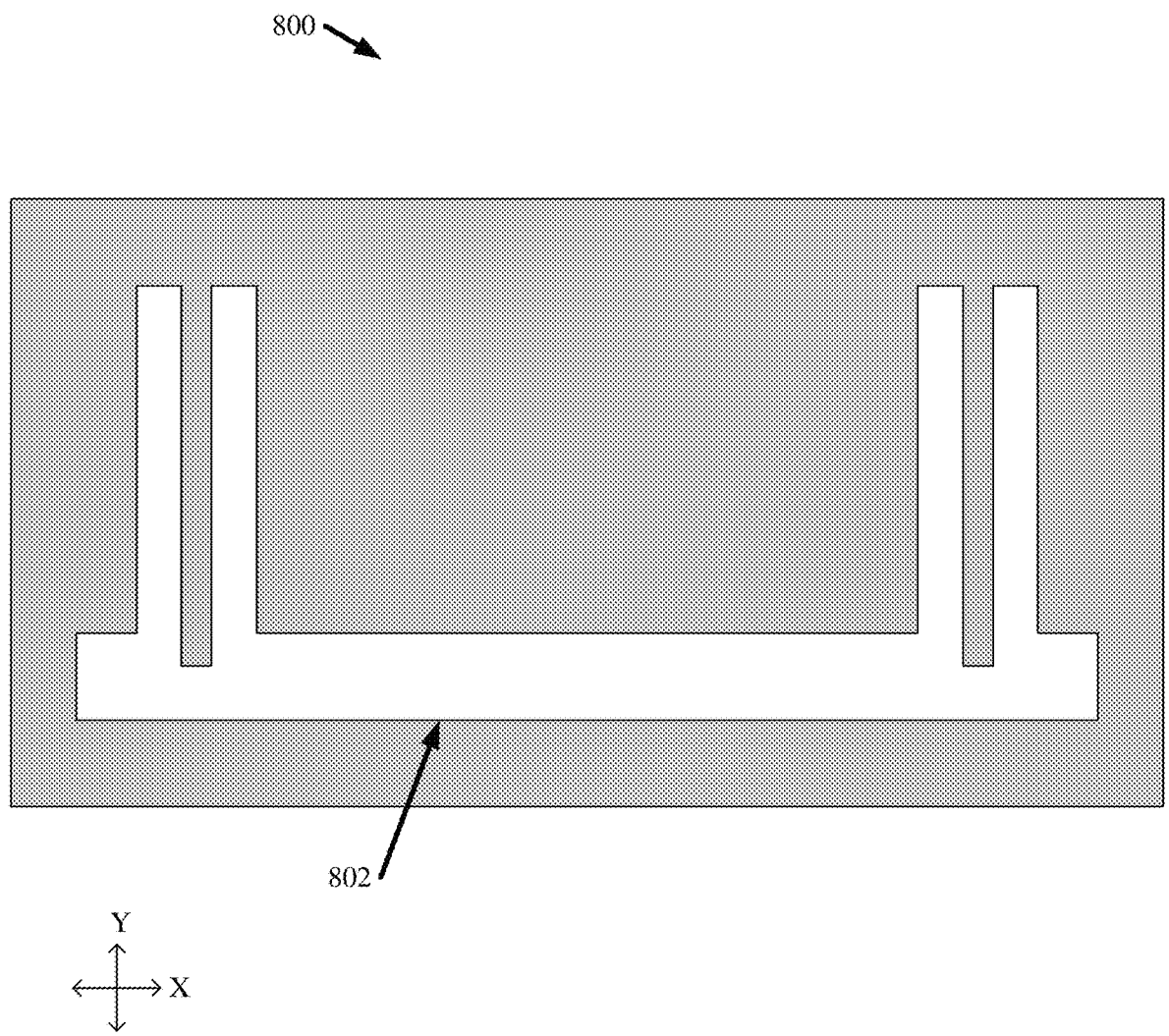
FIG. 8 illustrates a diagram of an example, non-limiting mold that can facilitate manufacturing of one or more biosensor packages in accordance with one or more embodiments described herein.

FIG. 8 illustrates a diagram of an example, non-limiting, cross-sectional view of an injection mold 800 that can facilitate manufacturing of the one or more biosensor packages 100 in accordance with one or more embodiments described herein. Repetitive description of like elements employed in other embodiments described herein is omitted for sake of brevity.

As shown in FIG. 8, the injection mold 800 can comprise one or more cavities 802 into which the elastomeric polymer can be injected to form the polymer layer 102. Thus, the dimensions of the one or more cavities 802 can depend on the desired dimensions of the polymer layer 102. Further, the one or more cavities 802 can define the one or more microfluidic channels that can comprise the one or more chemical delivery systems 106. One of ordinary skill in the art will readily recognize that the structure of the injection mold 800 can be designed to facilitate a polymer layer 102 architecture in accordance with one or more embodiments described herein (e.g., an architecture that can comprise a plurality of pockets 502, which can house an array of biosensor modules 104).

Figure 9:
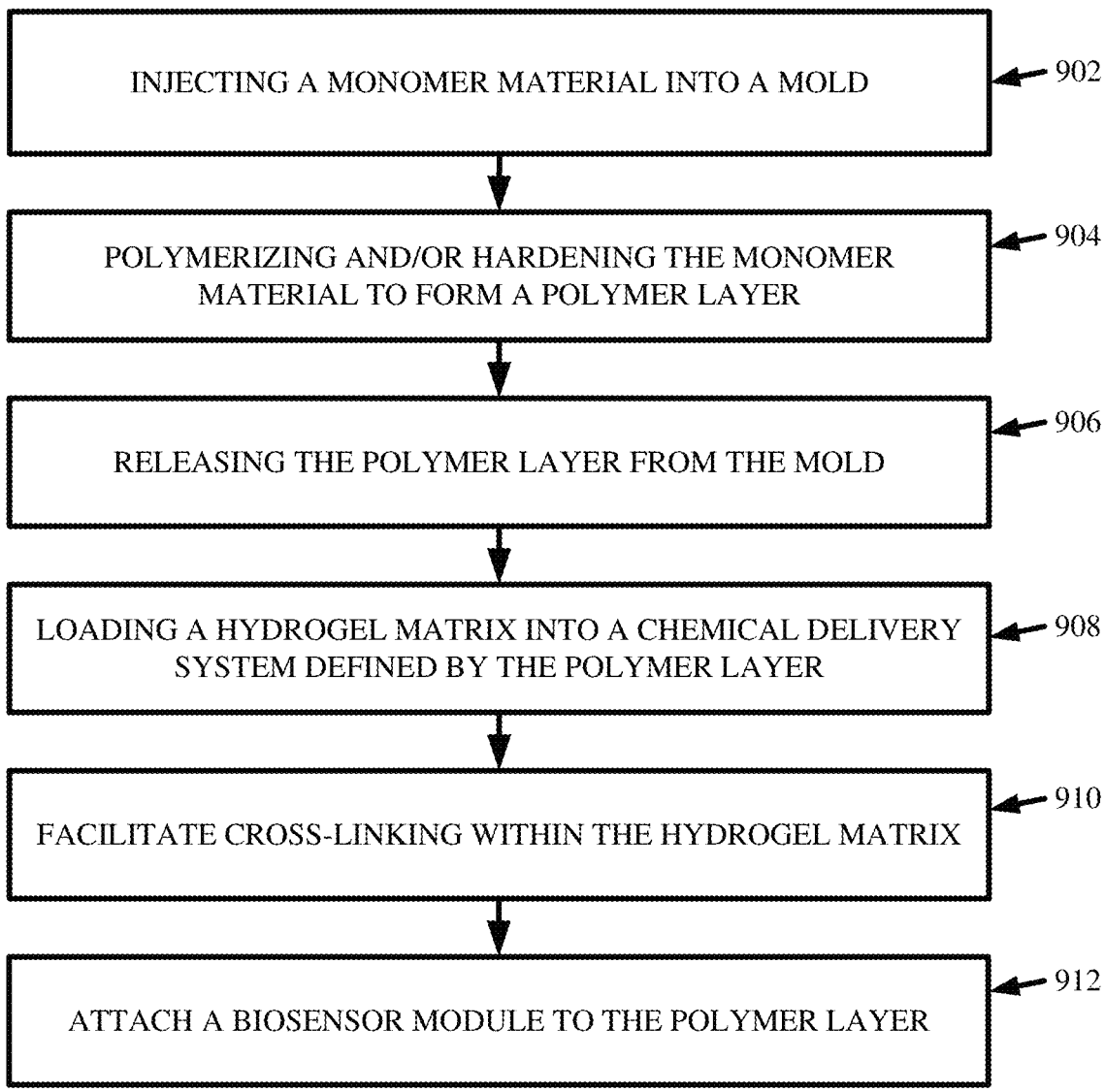
FIG. 9 illustrates a flow diagram of an example, non-limiting method that can facilitate manufacturing of one or more biosensor packages in accordance with one or more embodiments described herein.

FIG. 9 illustrates a flow diagram of an example, non-limiting method 700 that can facilitate manufacturing of one or more biosensor packages 100 in accordance with one or more embodiments in accordance with one or more embodiments described herein. Repetitive description of like elements employed in other embodiments described herein is omitted for sake of brevity.

At 902, the method 900 can comprise injecting a monomer material into a mold (e.g., injection mold 800). The monomer material can polymerize to form the polymer material that can comprise the polymer layer 102 in accordance with one or more embodiments. For example, the monomer material can comprise PDMS monomer, isocyanate monomers, and/or polyol monomers.

At 904, the method 900 can comprise polymerizing and/or hardening the monomer material to form the polymer layer 102. The polymerization and/or hardening at 902 can be facilitated by means of heat and/or light exposure of the monomer material while in the mold (e.g., injection mold 800). As described herein, the resulting polymer layer 102 can be characterized as durable, elastomeric, and bioinert.

At 906, the method 900 can comprise releasing the polymer layer 102 from the mold (e.g., injection mold 800). Releasing the polymer layer 102 from the mold (e.g., injection mold 800) can facilitate further manufacturing of the biosensor package 100.

At 908, the method 900 can comprise loading a hydrogel matrix (e.g., comprising hyaluronic acid polymer) into one or chemical delivery systems 106, which can be defined by the polymer layer 102. The hydrogel matrix can be embedded with one or more chemical compounds, including, but not limited to: a genetic material (e.g., carried by a virus) for expression of a protein, a neural transmitter (e.g., dopamine, gamma-Aminobutyric acid ("GABA"), and/or serotonin), a growth factor, a growth inhibitor, a medicine (e.g., a medication for epilepsy and/or Parkinson's disease), a combination thereof, and/or the like.

At 910, the method 900 can comprise facilitating cross-linking within the hydrogel matrix to achieve one or more compositional states that can help the hydrogel maintain within the one or more chemical delivery systems 106 until degradation (e.g., dissolution) by a bioenvironment. For example, the cross-linkage at 910 can be activated by heat and/or light exposure.

At 912, the method 900 can comprise attaching one or more biosensor modules 104 to the polymer layer 102. The one or more biosensor modules 104 can comprise, for example: one or more sensors 108, one or more semiconductor substrates 110, one or more stimulus devices 112, one or more computer units 114 (e.g., which can include one or more processors), and/or one or more power devices 116. Further, one or more of the features of the one or more biosensor modules 104 (e.g., the one or more sensors 108 and/or the one or more computer units 114) can be operably coupled together. In one or more embodiments, the one or more biosensor modules 104 can be inserted and/or attached to one or more pockets 502 defined by the polymer layer 102.

Figure 10:
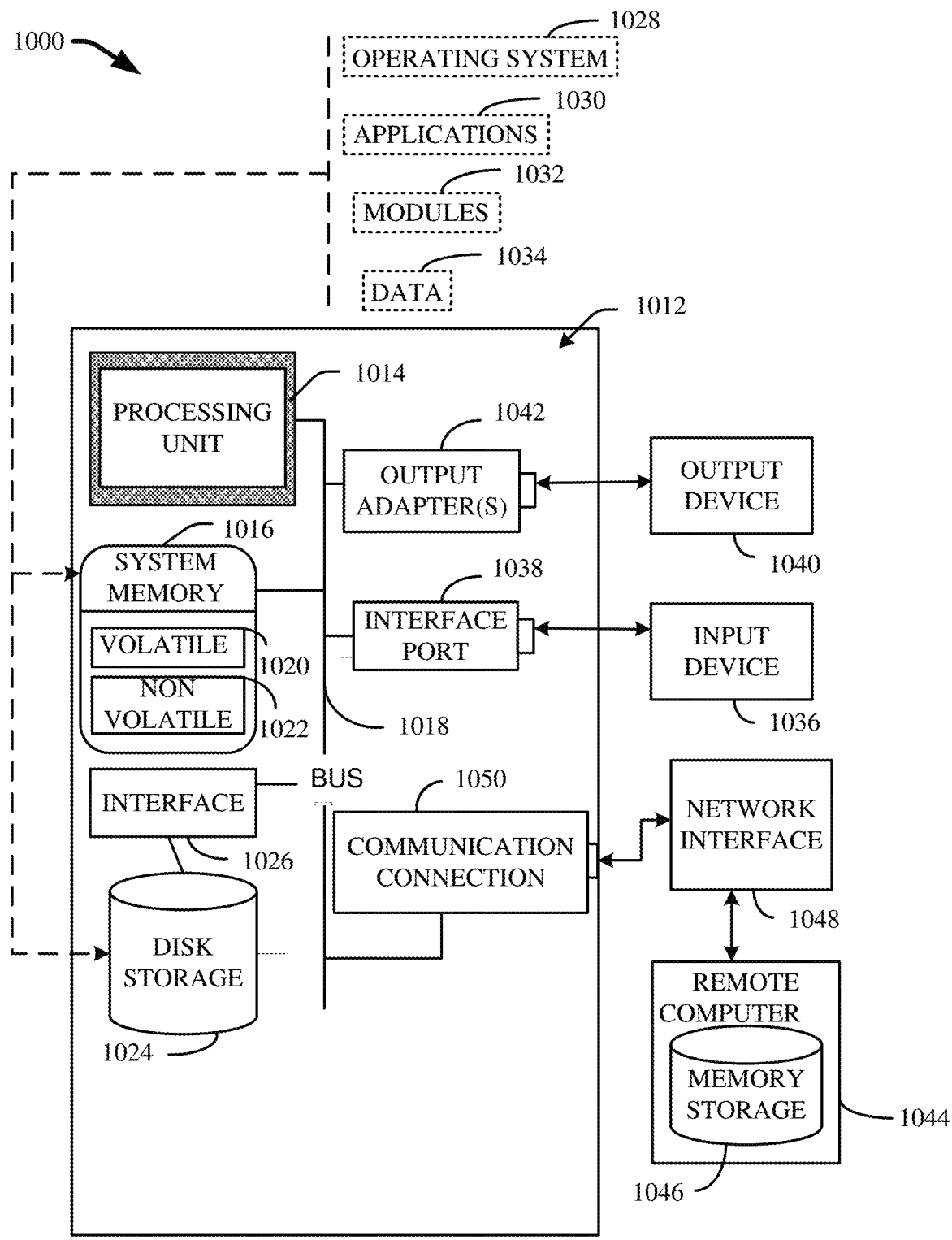
FIG. 10 illustrates a block diagram of an example, non-limiting operating environment in which one or more embodiments described herein can be facilitated.

In order to provide a context for the various aspects of the disclosed subject matter, FIG. 10 as well as the following discussion are intended to provide a general description of a suitable environment in which the various aspects of the disclosed subject matter can be implemented. FIG. 10 illustrates a block diagram of an example, non-limiting operating environment in which one or more embodiments described herein can be facilitated. For example, FIG. 10 depicts various features that can characterize the one or more computer units 114 and/or the one or more controllers 602. Repetitive description of like elements employed in other embodiments described herein is omitted for sake of brevity. With reference to FIG. 10, a suitable operating environment 1000 for implementing various aspects of this disclosure can include a computer 1012. The computer 1012 can also include a processing unit 1014, a system memory 1016, and a system bus 1018. The system bus 1018 can operably couple system components including, but not limited to, the system memory 1016 to the processing unit 1014. The processing unit 1014 can be any of various available processors. Dual microprocessors and other multiprocessor architectures also can be employed as the processing unit 1014. The system bus 1018 can be any of several types of bus structures including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire, and Small Computer Systems Interface (SCSI). The system memory 1016 can also include volatile memory 1020 and nonvolatile memory 1022. The basic input/output system (BIOS), containing the basic routines to transfer information between elements within the computer 1012, such as during start-up, can be stored in nonvolatile memory 1022. By way of illustration, and not limitation, nonvolatile memory 1022 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1020 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1012 can also include removable/non-removable, volatile/non-volatile computer storage media. FIG. 10 illustrates, for example, a disk storage 1024. Disk storage 1024 can also include, but is not limited to, devices like a magnetic disk drive, floppy disk drive, tape drive, Jaz drive, Zip drive, LS-100 drive, flash memory card, or memory stick. The disk storage 1024 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1024 to the system bus 1018, a removable or non-removable interface can be used, such as interface 1026. FIG. 10 also depicts software that can act as an intermediary between users and the basic computer resources described in the suitable operating environment 1000. Such software can also include, for example, an operating system 1028. Operating system 1028, which can be stored on disk storage 1024, acts to control and allocate resources of the computer 1012. System applications 1030 can take advantage of the management of resources by operating system 1028 through program modules 1032 and program data 1034, e.g., stored either in system memory 1016 or on disk storage 1024. It is to be appreciated that this disclosure can be implemented with various operating systems or combinations of operating systems. A user enters commands or information into the computer 1012 through one or more input devices 1036. Input devices 1036 can include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices can connect to the processing unit 1014 through the system bus 1018 via one or more interface ports 1038. The one or more Interface ports 1038 can include, for example, a serial port, a parallel port, a game port, and a universal serial bus (USB). One or more output devices 1040 can use some of the same type of ports as input device 1036. Thus, for example, a USB port can be used to provide input to computer 1012, and to output information from computer 1012 to an output device 1040. Output adapter 1042 can be provided to illustrate that there are some output devices 1040 like monitors, speakers, and printers, among other output devices 1040, which require special adapters. The output adapters 1042 can include, by way of illustration and not limitation, video and sound cards that provide a means of connection between the output device 1040 and the system bus 1018. It should be noted that other devices and/or systems of devices provide both input and output capabilities such as one or more remote computers 1044.

Computer 1012 can operate in a networked environment using logical connections to one or more remote computers, such as remote computer 1044. The remote computer 1044 can be a computer, a server, a router, a network PC, a workstation, a microprocessor based appliance, a peer device or other common network node and the like, and typically can also include many or all of the elements described relative to computer 1012. For purposes of brevity, only a memory storage device 1046 is illustrated with remote computer 1044. Remote computer 1044 can be logically connected to computer 1012 through a network interface 1048 and then physically connected via communication connection 1050. Further, operation can be distributed across multiple (local and remote) systems. Network interface 1048 can encompass wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). One or more communication connections 1050 refers to the hardware/software employed to connect the network interface 1048 to the system bus 1018. While communication connection 1050 is shown for illustrative clarity inside computer 1012, it can also be external to computer 1012. The hardware/software for connection to the network interface 1048 can also include, for exemplary purposes only, internal and external technologies such as, modems including regular telephone grade modems, cable modems and DSL modems, ISDN adapters, and Ethernet cards.

Embodiments of the present invention can be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which includes one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure can also be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components including a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems, computer program products and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An apparatus, comprising:
 a polymer layer comprising pockets formed in an array;
 at least one microfluidic channel formed between at least two of the pockets and comprising at least one chemical reagent for delivering in vivo; and
 biosensor device modules embedded within the pockets, wherein the biosensor device modules respectively comprise a semiconductor substrate with electrical components formed thereon, the electrical components comprising a processor and at least one sensor operably coupled to the processor, and wherein the polymer layer is embedded with stable bio molecules selected to provide camouflage against an immune system.

2. The apparatus of claim 1, wherein the stable bio molecules are selected from a group consisting of glycoproteins and myelin.

3. The apparatus of claim 1, wherein the polymer layer is elastomeric.

4. The apparatus of claim 3, wherein the polymer layer comprises a polymer selected from a second group consisting of polydimethylsiloxane, chitin, cellulose, and polyurethane.

5. The apparatus of claim 1, wherein the electrical components further comprise a light emitting diode operably coupled to the processor.

6. The apparatus of claim 5, wherein the semiconductor substrate is transparent, and wherein the light emitting diode is integrated into the semiconductor substrate.

7. The apparatus of claim 1, wherein the electrical components further comprise a power device selected from the group consisting of a capacitor and a battery.

8. The apparatus of claim 1, wherein the biosensor modules comprise at least two optogenetic stimulation device modules.

9. The apparatus of claim 1, wherein the biosensor modules comprise two or more of the same type of biosensor device module configured to perform a same electrical function.

10. The apparatus of claim 1, wherein the biosensor modules comprise two or more different types of biosensor modules respectively configured to perform different electrical functions.

11. An apparatus comprising:
- a polymer layer comprising pockets separated by microfluidic channels comprising at least one chemical substance for delivering in vivo; and
- biosensor modules embedded within the pockets, the biosensor modules respectively comprising electrical devices formed on a semiconductor substrate, the electrical devices comprising a processor, and an integrated stimulus device operably coupled to the processor, wherein the polymer layer is embedded with stable bio molecules selected to provide camouflage against a biological defense mechanism.

12. The apparatus of claim 11, wherein the semiconductor substrate is selected from the first group consisting of gallium nitride, silicon, sapphire, and silicon oxide, and wherein the polymer layer comprises a polymer selected from the second group consisting of polydimethylsiloxane and polyurethane.

13. The apparatus of claim 11, wherein the electrical devices further comprise a sensor and a power device, and wherein the sensor and the power device are operably coupled to the processor.

14. The apparatus of claim 11, wherein the at least one chemical substance is selected from the group consisting of a genetic material for expression of a protein, a neural transmitter, a growth factor, a growth inhibitor, and a medicine.

15. The apparatus of claim 11, wherein the electrical devices further comprise two or more devices selected from the group consisting of, a light emitting diode, a heater, an electrode and a power device.

16. The apparatus of claim 11, wherein the biosensor modules comprise two or more of the same type of biosensor module configured to perform a same electrical function.

17. The apparatus of claim 11, wherein the biosensor modules comprise two or more different types of biosensor modules respectively configured to perform different electrical functions.

18. The apparatus of claim 11, wherein the electrical devices further comprise a sensor and wherein at least two of the biosensor devices comprise different types of sensors.

19. The apparatus of claim 18, wherein the different types of sensors are selected from the group consisting of: a thermometer, a piezoelectric material, a light sensor, a pressure sensors, an electrode, a chemical sensor, a field-effect transistor sensor, a bipolar junction transistor sensor, a conductive organic electrode imprinted with a target molecule, an organic electrochemical transistor device, and a fluorescence detector.

20. The apparatus of claim 11, wherein the pockets respectively have a length of about 1000 micrometers or less.

* * * * *